United States Patent [19]

Buchholz et al.

[11] Patent Number: 5,026,915
[45] Date of Patent: Jun. 25, 1991

[54] PROCESS FOR THE MANUFACTURE OF DIALKYL DISULFIDES

[75] Inventors: Bernard Buchholz, Whitpain; Edward J. Dzierza, Philadelphia; John R. Baltrus, Whitpain, all of Pa.

[73] Assignee: Atochem North America, Inc., Philadelphia, Pa.

[21] Appl. No.: 496,044

[22] Filed: Mar. 16, 1990

Related U.S. Application Data

[63] Continuation of Ser. No. 312,511, Feb. 17, 1989, abandoned, which is a continuation of Ser. No. 733,551, May 13, 1985, abandoned.

[51] Int. Cl.$^5$ ............................................. C07C 319/24
[52] U.S. Cl. ............................................. 568/26; 568/71
[58] Field of Search .................. 568/26, 21, 59, 60, 568/71

[56] References Cited

U.S. PATENT DOCUMENTS

| | | | |
|---|---|---|---|
| 3,022,351 | 2/1962 | Mihm et al. | 568/26 |
| 3,035,097 | 5/1962 | Deger et al. | 568/71 |
| 3,314,999 | 4/1967 | Bapseres et al. | 568/26 |
| 3,755,461 | 8/1973 | Kvasnikoff et al. | 568/26 |
| 4,302,605 | 11/1981 | Buchholz et al. | 568/60 |
| 4,313,006 | 1/1982 | Hager | 568/70 |
| 4,396,778 | 8/1983 | Hager | 568/70 |
| 4,564,709 | 11/1986 | Koyama et al. | 568/26 |

FOREIGN PATENT DOCUMENTS 159456  9/1983  Japan.

OTHER PUBLICATIONS

K. Liu, Synthesis, Sep. '78, (9) pp. 669–670, "A Facile Conversion of Thiols to Disulfides".
E. E. Reid, "Organic Chemistry of Bivalent Sulfur", vol. 1, pp. 118–126 (1958).

*Primary Examiner*—Mary E. Ceperley

[57] ABSTRACT

A continuous process is disclosed for preparing dialkyl disulfides by reacting an alkyl alcohol and hydrogen sulfide in one reaction zone, and then passing the reactor effluent into a second reaction zone where it is reacted with elemental sulfur in the presence of a solid, particulate catalyst.

10 Claims, 1 Drawing Sheet

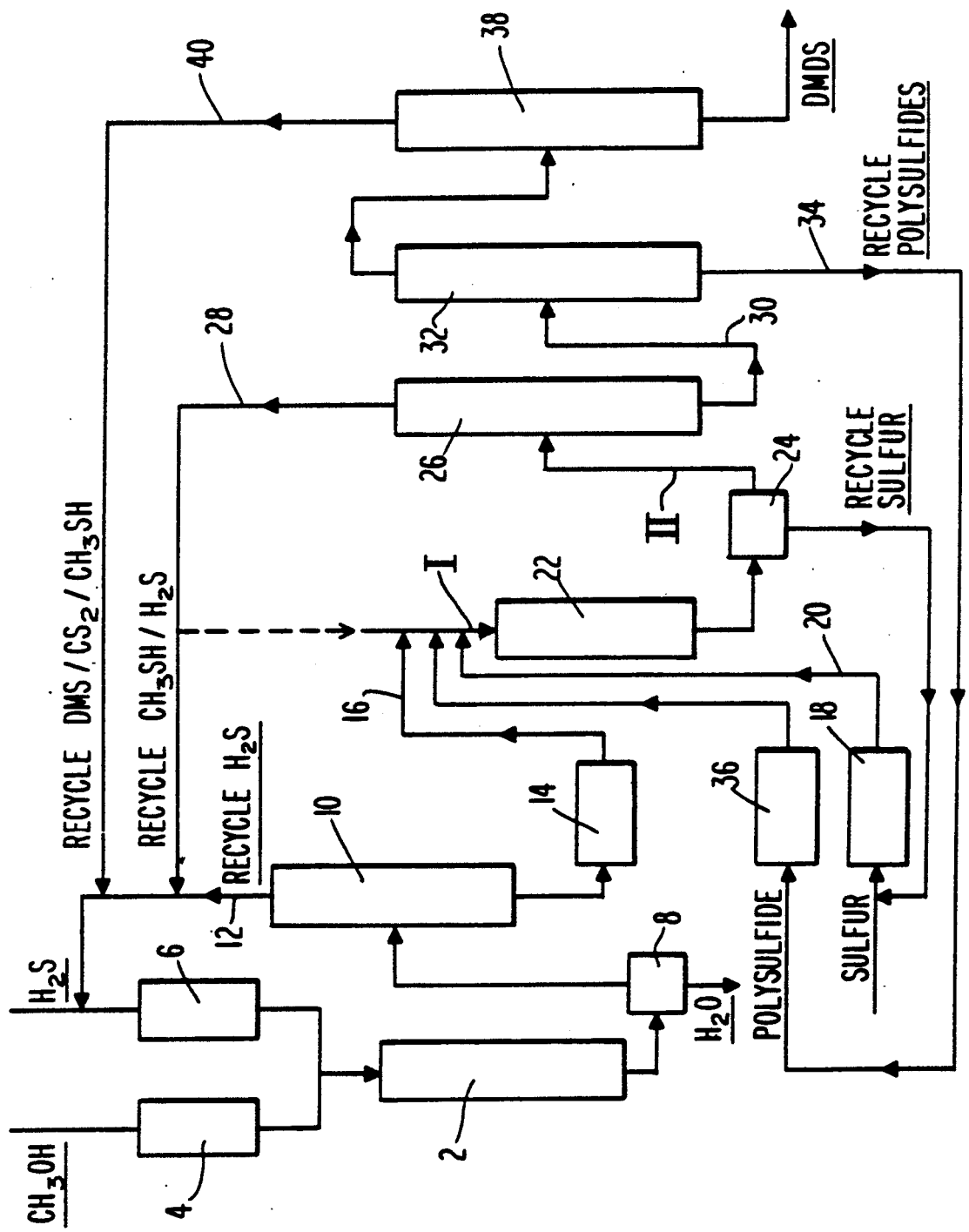

PROCESS FOR THE MANUFACTURE OF DIALKYL DISULFIDES

This is a continuation of copending application(s) Ser. No. 0/312,511 filed Feb. 17, 1989, now abandoned, which is a continuation of Ser. No. 733,551 filed May 13, 1985, now abandoned.

BACKGROUND OF THE INVENTION

This invention relates to a continuous process for the manufacture of dialkyl disulfides by reacting an alkyl alcohol with hydrogen sulfide over a solid, particulate catalyst, in one reactor zone and then passing the reactor effluent into a second reaction zone, where it is reacted as a vapor with elemental molten sulfur in the presence of the same or different solid, particulate catalyst. More particularly, it relates to a two-reactor process for the continuous manufacture of a dialkyl disulfide from a $C_1$–$C_{12}$ alkyl alcohol, hydrogen sulfide, and sulfur, in the presence of solid particulate catalysts.

The process reactions are represented by the following equations:

$$\text{catalyst(1)} \quad 2ROH + 2H_2S \rightarrow 2RSH + 2H_2O \text{(reactor 1)}$$

$$\text{catalyst(2)} \quad 2RSH + S \rightarrow RSSR + H_2S \text{(reactor 2)}$$

$$2ROH + H_2S + S \rightarrow RSSR + 2H_2O \text{(overall process)} \qquad (3)$$

When R is methyl, for example, the process can be utilized to prepare dimethyl disulfide (DMDS) from methanol, hydrogen sulfide, and elemental sulfur, according to equation (3) above. DMDS is a well known article of commerce, being used as a sulfiding agent for the pre-treatment and post-regenerative treatment of hydro-desulfurization catalysts in petroleum refining, as a down-hole sulfur solvent for oil wells, and as a chemical intermediate in the manufacture of agricultural compounds in lieu of methyl mercaptan.

PRIOR ART

It is known that disulfides are produced by the oxidation of mercaptans with sulfur, according to equation (4), especially in the presence $$2RSH + S \rightarrow RSSR + H_2S \qquad (4)$$

(R = alkyl or aryl)
of alkali, ammonia, or an amine (E. E. Reid, *Organic Chemistry of Bivalent Sulfur*, Volume 1, p. 121, Chemical Publishing Co., Inc., New York (1958). The liquid-phase reaction of mercaptans with sulfur as the oxidizing agent using alkali or amine catalysts is reported in U.S. Pat. Nos. 3,314,999 and 3,755,461. In the above method, it is first necessary to manufacture and isolate the mercaptan before oxidizing it with sulfur to the corresponding disulfide.

Processes for the manufacture of mercaptans from alcohols and hydrogen sulfide, according to equation (5), where R is alkyl $$ROH + H_2S \rightarrow RSH + H_2O \qquad (5)$$

or aryl, are known and shown, for example, in U.S. Pat. No. 3,035,097.

STATEMENT OF THE INVENTION

This invention is a method for manufacturing di($C_1$–$C_{12}$)alkyl disulfides in a continuous process comprising continuously reacting a $C_1$–$C_{12}$ alkyl alcohol and hydrogen sulfide in a molar ratio of 1:2 to 1:20 in contact with a solid, particulate catalyst in a first reaction zone at a temperature ranging from about 100° C. to about 500° C. and then continuously passing the crude mercaptan product of the reaction and molten sulfur at a molar ratio of from 1:0.05 to 1:2 in contact with a solid, particular catalyst in a second reaction zone at a temperature ranging from about 125° C. to about 400° C., and recovering di ($C_1$–$C_{12}$) alkyl disulfide.

DISCUSSION OF THE INVENTION

A method of manufacturing dialkyl disulfides in a continuous, two-reactor process, using solid particulate catalysts in each reactor, has been found which process possesses an improved selectivity for the formation of dialkyl disulfides from alkyl alcohols, hydrogen sulfide, and sulfur.

One advantage of this process over prior art processes is that it produces dialkyl disulfides from alkyl alcohols, rather than alkyl mercaptans, as a raw material, resulting in a substantial cost savings. Another advantage of this process is that the dialkyl disulfides can be manufactured with very little formation of unwanted byproduct dialkyl sulfides or carbon disulfide. Still another advantage is that the dialkyl polysulfides, which are formed as byproducts in this process, can be totally recycled to the second reactor where they react with the intermediate alkyl mercaptan to form additional dialkyl disulfide. Still another advantage is that high dialkyl disulfide production rates can be sustained for long periods of time without the necessity for periodic air-regeneration of the catalyst to remove coke and tars.

The $C_1$–$C_{12}$ alkyl alcohols used in the process of this invention include, for example, methanol, ethanol, propanol, butanol, pentanol, hexanol, heptanol, octanol, decanol, dodecanol and isomeric forms of these normal alcohols. Preferably, the $C_1$–$C_6$ alkyl alcohols are used in the process, more preferably the $C_1$–$C_4$ alkanols and most preferably, methanol.

Any of a variety of solid, particulate catalysts, preferably aluminum-containing catalysts, are used in both of the reaction zones of the process of this invention. Alumina, silica, thoria, or alumina promoted with an alkali metal tungstate or alumina promoted with an alkali metal heteropoly acid salt, such as potassium phosphotungstate, can be used to convert the $C_1$ to $C_{12}$ alkyl alcohol to $C_1$ to $C_{12}$ alkyl mercaptan. The catalysts described at column 2, line 43 through a column 4, line 24 of U.S. Pat. No. 3,035,097 are some of the catalysts suitable for this invention and this portion of the '097 patent is incorporated herein by reference.

The aluminum-containing catalysts of the second reaction-zone, are preferably synthetic aluminosilicates characterized by high uniformity, well-defined pore size, large surface area, and complete crystallinity. The structures of the zeolite catalysts are described in Union Carbide's booklet F-08 entitled "*Zeolite Molecular Sieve Catalysts*" and D. W. Breck, *Zeolite Molecular Sieves*, (1974), John Wiley & Sons, New York. Various types of zeolite catalysts are manufactured, for example, by Akzo Chemie, Air Products (Houdry), Norton, PQ Corporation, United Catalysts, and Union Carbide.

The basic unit of the synthetic zeolites is composed of silicon and aluminum atoms tetrahedrally coordinated with four oxygen atoms. Since the aluminum atoms are trivalent, they have a net negative charge when bonded with 4 oxygen atoms (AlO4−). This charge is balanced by a cation, such as Na+, K+, or H+ in the as-synthesized zeolites. These cations can be exchanged with other metals or cations. For example, a divalent cation such as cobalt will replace 2 univalent cations, while a trivalent cation such as chromium, lanthanum, or cerium will replace 3 univalent cations. It is thus possible to replace the alkali metal cations, Na+ or K+, with catalytically more active cations such as Ag+1, Co+2, Ni+2, Mo+2 (or+3), Fe+2 (or+3), Cr+3, La+3, etc., if desired. However, the alkali metal cations are preferred for this invention, with the catalyst typically containing about 13 percent by weight of the alkali metal, expressed as the alkali metal oxide (eg., $Na_2O$, $K_2O$).

Although many factors influence the catalytic activity of these zeolites, the three most important are, (1) the open framework structure with its attendant pore size, (2) the $SiO_2:Al_2O_3$ ratio of the framework, and (3) the cations. As in most catalytic processes, the large-pore zeolites having pore openings in the range of 7 to 10 Angstroms are most useful. The most preferred are Type X, Type Y, and Type L zeolites. Type X has a chemical composition expressed in terms of oxide ratios of $Na_2O:Al_2O_3:2-3SiO_2$ with a typical unit cell composition in the hydrated state of $Na_{86}$ $[AlO_2)_{86}(SiO_2)_{106}]\cdot 264\ H_2O$. Type Y, on the other hand, has a composition of $Na_2O:Al_2O_3:>3-6\ SiO_2$. When the $SiO_2:Al_2O_3$ molar ratio is 4.8, the hydrated unit cell composition is $Na_{56}$ $[(AlO_2)_{56}(SiO_2)_{136}]\cdot 264\ H_2O$. Type L, more siliceous then Type X and Type Y, also has a pore size in the 7 to 10 Angstrom range.

An important building block of these zeolites is the sodalite cage, a truncated octahedron unit consisting of 24 $(SiO_4,AlO_4)$ units. In Type X and Type Y zeolites, the sodalite cages are connected through 4 of the 8 hexagonal faces in a tetrahedral arrangement. The pores thus created are defined by a 12-member ring of oxygen atoms, approximately 7 to 9 Angstroms in size, opening into a central cavity of about 11 Angstroms in diameter.

The more preferred synthetic zeolites are Types X and Y because of their larger pore sizes. The ability of the Type Y to withstand higher temperatures without losing its crystalline structure makes it the most preferred zeolite catalyst for the second reaction zone of this invention.

The zeolites, as prepared, generally contain as the cation about 13 percent by weight sodium (as $Na_2O$) or equivalent amount of other alkali metal (as $Me_2O$). As explained above, this cation may be replaced with other cations to reduce the sodium content. In this invention, however, the most preferred catalyst contains sodium as the cation, with a sodium content of at least 3 percent, preferably more than 5 percent, more preferably greater than 10 percent, and most preferably at the 13 percent by weight (as $Na_2O$) level.

THE DRAWING

An example of the process of this invention is depicted in the drawing which is a flow diagram for the manufacture of dialkyl disulfide represented by dimethyl disulfide (DMDS).

Methanol and hydrogen sulfide are fed continuously in a molar ratio ranging from about 1:2 to 1:20, preferably from 1:6 to 1:10 to a first reactor 2, the excess hydrogen sulfide being used to depress the formation of by-product dimethyl sulfide. The reactants are heated and vaporized in preheaters 4 and 6, mixed, and charged to reactor 2 wherein the reaction takes place in the presence of a solid, particulate catalyst, e.g., alumina with or without potassium phosphotungstate promoter, at a pressure ranging between atmospheric and 500 psig, preferably between about 100 and 400 psig, and at a temperature ranging from about 100° to about 500° C., preferably from about 250° to about 400° C. The reaction temperature is determined by the catalyst bed temperature. The molar velocity of the alcohol may vary over a wide range but will usually be between about 50 and 500, preferably between about 100 and 150, gram-moles of alcohol vapor per kilogram of catalyst per 24 hours (at STP). The volume of the catalyst in the first reaction zone is adjusted to produce mercaptan at the desired rate for passage of the crude mercaptan to the second reaction zone.

Most of the byproduct water is removed in the liquid-phase water-separator 8. A major portion of the hydrogen sulfide in the effluent from reactor 2 is separated from the effluent mixture in high pressure separator 10 and returned via line 12 to reactor 2. Crude mercaptan in the effluent stream passing from the bottom of separator 10 is preheated at 14 and forwarded through line 16 to the second reactor. Fresh sulfur is also introduced to the second reactor through preheater 18 via line 20. Molten sulfur is fed to second reactor 22 in a molar ratio that is preferably about 0.15 for each mole of mercaptan which provides less sulfur than is required to meet the stoichiometric requirement for the equation:

$$2CH_3SH + S \rightarrow CH_3SSCH_3 + H_2S$$

This sulfur deficiency minimizes polysulfide formation. The preheated reactants are mixed, at point I, and charged to the reactor 22 wherein they are subjected to elevated temperatures in the range of 125° to 250° C. and pressures from atmospheric to about 600 psig in the presence of a particulate catalyst, preferably a Type X or Y zeolite, to effect reaction. Under the stated conditions, the crude methyl mercaptan is in the vapor phase and the elemental sulfur is in the liquid phase.

Any unreacted sulfur is separated in a knock-out pot 24 from the crude product issuing from the bottom of reactor 22. After sulfur separation, the crude product is passed into a series of distillation columns (or towers). The first column 26 removes the low-boilers (largely unreacted methyl mercaptan and $H_2S$) through the overhead stream 28 and recycles them back to the reactor 2 or, alternatively, reactor 22. The bottoms stream is then passed via line 30 to the second distillation tower 32 where the heavies, mostly polysulfides, are taken as bottoms and recycled through heater 36 back to second reactor 22 to react with the mercaptan to form more disulfide (e.g., $CH_3SSSCH_3 + 2CH_3SH \rightarrow 2CH_3SSCH_3 + H_2S$). The remaining low-boilers, e.g., minor amounts of dimethyl sulfide and carbon disulfide, and the product, DMDS, are taken as an overhead and passed to the third tower 38. The high-purity product DMDS, is taken off from tower 38 as a bottoms material, while the low-boilers are taken overhead through line 40 for recycle back to the first reactor 2.

Operable conditions for the desired reaction to occur in the reactor 22 are the presence of a solid, particulate catalyst, a catalyst bed temperature in the range 125°–400° C., and pressures ranging from atmospheric to 600 psig. The molar ratio of fresh sulfur and crude alkyl mercaptan from reactor 2 fed to the second reactor 22 may range from a 2 to 1 molar excess of sulfur over alkyl mercaptan to a 20 to 1 molar excess of alkyl mercaptan over sulfur. The molar ratios in the combined fresh-plus-recycle feed to the reactor 22 may, of course, be outside this range and will usually contain a substantial molar excess of alkyl mercaptan over sulfur, which may be as high as 20 to 1, to avoid excess polysulfide formation. The feed to the reactor 22 may also contain up to 50 percent by volume of an inert gas or mixture of inert cooling gases to provide sufficient heat removal from the catalyst zone. The inert gases may be nitrogen, methane, ethane, propane, butane, carbon dioxide, or any other gas that does not interfere with the reactions to produce the desired dialkyl disulfide. The rate at which the crude alkyl mercaptan is passed over the catalyst may range from about 100 to about 2000 gram-moles of alkyl mercaptan per kilogram of catalyst per 24 hours, or expressed in different units, from 100 to about 2000 pound-moles per 1000-pounds of catalyst per 24-hour day.

The preferred catalyst-bed temperatures (catalyst bed temperature equals reaction temperature) in reactor 22 are in the range 125°–225° C., and the preferred pressures are in the range 50–375 psig. The preferred molar ratio of crude alkyl mercaptan to sulfur fed into reactor 22 is in the range 20/1 to 1/1, and is most preferably near the molar ratio of about 7/1. The preferred rate at which the crude alkyl mercaptan is passed over the catalyst is in the range 750–1250 gram-moles of alkyl mercaptan per kilogram of catalyst per 24 hours. The preferred catalyst is a Type Y zeolite having a sodium content of about 13% by weight, expressed as $Na_2O$.

The following examples omit the first phase reaction of this process wherein methyl mercaptan is produced substantially in accordance with the process disclosed in U.S. Pat. No. 3,035,097 from methyl alcohol and hydrogen sulfide. Instead, a simulated crude product of the first phase reaction consisting of methyl mercaptan and hydrogen sulfide is fed to the second stage reactor along with sulfur (with and without recycle polysulfides) in the prescribed molar ratio. In the example, 14 runs are made to demonstrate the process of this invention using a Type Y zeolite catalyst containing 13 weight percent sodium expressed as $Na_2O$. The composition of the crude product, sampled at point II of the flow diagram of the Drawing, is determined by gas chromatographic (GC) analysis. The material balances across reactor 22, and the single-pass conversions of the crude methyl mercaptan to DMDS are calculated from the GC data.

EXAMPLE 1

To simulate a fresh-plus-recycle feed mixture of the process, as indicated at point I of the flow diagram of the Drawing, when all byproduct dimethyl polysulfides are recycled, methyl mercaptan, $H_2S$, sulfur, and an approximately 80/20 by weight mixture of dimethyl trisulfide and dimethyl tetrasulfide, were pumped separately, as liquids, at appropriate rates to provide a continuous $CH_3SH/H_2S/S/DMS_x$ mixture in the desired molar ratios from 1/0.5/0.15/0.04 to 1/0.5/0.15/0.09.

The above reaction components were passed individually through stainless steel packed tubes installed in an electrically-heated preheater maintained at 200°–225° C. The liquid polysulfides (80/20 mix) were blended with the vaporized gases in a static mixer before entering the reactor tube. The molten sulfur was then injected into the gas stream at the top of the reactor tube. The reactor is a 316 stainless steel tube, 2 inches in diameter (i.d.), and 36 inches in length, enclosed in an electrically heated vertical furnace. The catalyst is a Type Y zeolite containing 13% by weight sodium, expressed as $Na_2O$, in the form of a ⅛ inch extrudate sold by Union Carbide under a product designation LZ-Y52. It is arranged in a 6–9 inch fixed bed located centrally within the vertical reactor tube and maintaned in the temperature range of 145° 14 165° C. The exit stream was passed as a vapor into a stainless steel vessel maintained at 165° C. to separate unreacted sulfur from the crude product stream. The effluent was then cooled by passing the crude product through a coil immersed in a cooling bath maintained at minus 5° C., such temperature being sufficient to completely liquify the crude reactor effluent. The liquified stream was then passed directly into a gas chromatograph for analysis. The stream was visually inspected to confirm complete liquification, passed through a back-pressure control-release valve and then into a closed-end vessel maintained at minus 50° C. The pressure in the reactor system was kept between 325 and 340 psig, and the methyl mercaptan molar-velocity was maintained at about 1000 gram-moles of $CH_3SH$ per kilogram of catalyst per 24 hours.

Two series of seven continuous runs (1–14), of approximately 12 hours duration each, were made using the Union Carbide LZ-Y52 sodium zeolite catalyst. The reaction conditions and production rates of the products are given in Table 1 for each run. A series of GC analyses of the effluent were made at point II of the Drawing during each run and averaged to obtain the production figures shown for each run. Other runs using the above described zeolite catalyst and varying process conditions are shown in Table 2 (Runs 15–23) and Table 3 (Runs 24–40).

Overall yields of DMDS, based on methanol, are calculated to be over 90% for this two-reactor process, with recycling, as illustrated in the Drawing, when operating at preferred conditions.

For the Type Y zeolite catalyst of high sodium content, Tables 1, 2, and 3 distinctly show the effect of operating conditions on the rate of product formation. In Table 1, the effect of the sulfur to methyl mercaptan ratio is clearly shown. On reducing the sulfur-to-mercaptan molar ratio to 0.2:1 or lower, no $CS_2$ by-product is produced. The conversion of methyl mercaptan to DMDS is calculated as the moles of DMDS produced times 2 divided by the moles of $CH_3SH$ fed. As shown in Table 1, 19 to 32 percent of the methyl mercaptan fed is converted in a single pass to DMDS, with no yield losses to dimethyl sulfide or $CS_2$. Although some of the conversions of methyl mercaptan to DMDS shown in Tables 2 and 3 are nearly equal to those shown in Table 1, the high production rate of byproduct $CS_2$, and the presence of dimethyl sulfide, shown in Tables 2 and 3, make the conditions employed less desirable.

EXAMPLE 2

Example 1 is repeated, except that the catalyst used is Union Carbide's LZ-Y62 protonated zeolite (about 2.5% sodium expressed as $Na_2O$) and, except for the high $H_2S$ levels used, the operating conditions are comparable to those in Tables 2 and 3. The high $H_2S$ for each run was needed to reduce coke formation. In run 44, the conversion reached the level of single-pass conversion (22%) observed with the LZ-Y52 catalyst, but the production levels of the undesirable byproducts $CS_2$ and dimethyl sulfide, increased to an unacceptable level. The catalyst was found to contain coke and tars on removal from the reactor. The results of runs (41-44) of this example are reported in Table 4.

EXAMPLE 3

Example 1 is repeated, except that the catalyst is a commercial alumina (Alcoa F-1) doped with 5% potassium hydroxide, based on the weight of the alumina, prepared by dissolving the KOH in water just sufficient to wet the catalyst, followed by oven drying. The operating conditions are comparable to those in Tables 2 and 3, in run 46, the level of single-pass conversion of methyl mercaptan to DMDS (30%) was equal to that observed during the runs of Example 1. The results of runs (45-48) of this example are reported in Table 5.

TABLE 1
(EXAMPLE 1)

| Run No. | Catalyst Bed Temp. | $CH_2SH$ Mole Velocity | $H_2S$ Mole Velocity | Sulfur Mole Velocity | Inerts Mole Velocity | Bottoms Mole Velocity | Gms. DMDS Produced | Gm. $CS_2$ Produced | Gm. DMS Produced | Per Cent Conversion to DMDS |
|---|---|---|---|---|---|---|---|---|---|---|
| 1  | 150 | 936  | 423 | 228 | 0 | 0  | 8591  | 259 | 0 | 20 |
| 2  | 151 | 932  | 437 | 237 | 0 | 0  | 9165  | 247 | 0 | 22 |
| 3  | 151 | 942  | 608 | 229 | 0 | 0  | 8199  | 326 | 0 | 20 |
| 4  | 148 | 970  | 578 | 255 | 0 | 0  | 9583  | 304 | 0 | 22 |
| 5  | 152 | 1029 | 555 | 244 | 0 | 52 | 12779 | 345 | 0 | 25 |
| 6  | 150 | 1070 | 494 | 250 | 0 | 67 | 15321 | 553 | 0 | 28 |
| 7  | 153 | 1098 | 499 | 242 | 0 | 66 | 15572 | 645 | 0 | 28 |
| 8  | 154 | 992  | 537 | 135 | 0 | 0  | 8970  | 0   | 0 | 19 |
| 9  | 162 | 1010 | 508 | 162 | 0 | 0  | 10840 | 0   | 0 | 23 |
| 10 | 160 | 999  | 487 | 216 | 0 | 0  | 12240 | 0   | 0 | 26 |
| 11 | 156 | 1000 | 523 | 211 | 0 | 0  | 10403 | 0   | 0 | 22 |
| 12 | 154 | 996  | 513 | 181 | 0 | 40 | 12504 | 0   | 0 | 27 |
| 13 | 149 | 1009 | 531 | 146 | 0 | 68 | 13450 | 0   | 0 | 28 |
| 14 | 152 | 998  | 513 | 146 | 0 | 91 | 15230 | 0   | 0 | 32 |

TABLE 2
(EXAMPLE 1)

| Run No. | Catalyst Bed Temp. | $CH_2SH$ Mole Velocity | $H_2S$ Mole Velocity | Sulfur Mole Velocity | Inerts Mole Velocity | Gms. DMDS Produced | Gm. $CS_2$ Produced | Gm. DMS Produced | Per Cent Conversion to DMDS |
|---|---|---|---|---|---|---|---|---|---|
| 15 | 203 | 200 | 400 | 200 | 50  | 2008 | 2700 | 170 | 21 |
| 16 | 169 | 200 | 400 | 200 | 50  | 2513 | 733  | 70  | 27 |
| 17 | 186 | 200 | 400 | 200 | 300 | 2500 | 1292 | 162 | 27 |
| 18 | 168 | 225 | 400 | 200 | 300 | 3351 | 582  | 50  | 31 |
| 19 | 160 | 203 | 400 | 200 | 300 | 2911 | 581  | 86  | 31 |
| 20 | 158 | 96  | 200 | 100 | 150 | 1019 | 510  | 68  | 22 |
| 21 | 151 | 88  | 800 | 100 | 0   | 14   | 1996 | 5   | 1  |
| 22 | 140 | 93  | 800 | 100 | 0   | 0    | 2065 | 0   | 0  |
| 23 | 166 | 222 | 400 | 200 | 300 | 449  | 4021 | 762 | 4  |

TABLE 3
(EXAMPLE 1)

| Run No. | Catalyst Bed Temp. | $CH_2SH$ Mole Velocity | $H_2S$ Mole Velocity | Sulfur Mole Velocity | Inerts Mole Velocity | Gms. DMDS Produced | Gm. $CS_2$ Produced | Gm. DMS Produced | Per Cent Conversion to DMDS |
|---|---|---|---|---|---|---|---|---|---|
| 24 | 167 | 208 | 400  | 245 | 400 | 384  | 542  | 46 | 4  |
| 25 | 168 | 200 | 400  | 243 | 400 | 876  | 543  | 10 | 9  |
| 26 | 166 | 206 | 400  | 215 | 400 | 1106 | 1213 | 2  | 11 |
| 27 | 165 | 204 | 400  | 220 | 400 | 1795 | 1587 | 0  | 19 |
| 28 | 165 | 202 | 400  | 179 | 400 | 2185 | 256  | 0  | 23 |
| 29 | 167 | 330 | 1335 | 362 | 400 | 1632 | 2945 | 0  | 11 |
| 30 | 167 | 308 | 1538 | 156 | 400 | 3232 | 1903 | 0  | 22 |
| 31 | 147 | 136 | 1000 | 62  | 300 | 544  | 462  | 0  | 8  |
| 32 | 136 | 140 | 1000 | 60  | 300 | 448  | 447  | 0  | 7  |
| 33 | 195 | 90  | 667  | 44  | 200 | 278  | 427  | 8  | 7  |
| 34 | 195 | 266 | 818  | 120 | 300 | 268  | 3618 | 0  | 2  |
| 35 | 136 | 178 | 545  | 66  | 200 | 904  | 752  | 0  | 11 |
| 36 | 195 | 267 | 818  | 107 | 300 | 1725 | 1052 | 0  | 14 |
| 37 | 135 | 273 | 818  | 109 | 300 | 1688 | 905  | 0  | 13 |
| 38 | 195 | 182 | 545  | 79  | 200 | 1229 | 956  | 0  | 14 |
| 39 | 135 | 86  | 667  | 41  | 200 | 277  | 230  | 0  | 7  |
| 40 | 195 | 139 | 1000 | 60  | 300 | 349  | 584  | 0  | 5  |

TABLE 4
(EXAMPLE 2)

| Run No. | Catalyst Bed Temp. | CH$_2$SH Mole Velocity | H$_2$S Mole Velocity | Sulfur Mole Velocity | Inerts Mole Velocity | Gms. DMDS Produced | Gm. CS$_2$ Produced | Gm. DMS Produced | Per Cent Conversion to DMDS |
|---|---|---|---|---|---|---|---|---|---|
| 41 | 264 | 100 | 800 | 100 | 0 | 12 | 0 | 220 | <1 |
| 42 | 264 | 100 | 800 | 420 | 0 | 152 | 2765 | 238 | 3 |
| 43 | 219 | 200 | 800 | 420 | 0 | 522 | 1198 | 93 | 6 |
| 44 | 207 | 300 | 800 | 420 | 0 | 3086 | 1881 | 344 | 22 |

TABLE 5
(EXAMPLE 3)

| Run No. | Catalyst Bed Temp. | CH$_2$SH Mole Velocity | H$_2$S Mole Velocity | Sulfur Mole Velocity | Inerts Mole Velocity | Gms. DMDS Produced | Gm. CS$_2$ Produced | Gm. DMS Produced | Per Cent Conversion to DMDS |
|---|---|---|---|---|---|---|---|---|---|
| 45 | 150 | 204 | 400 | 338 | 300 | 354 | 1703 | 91 | 4 |
| 46 | 190 | 204 | 400 | 400 | 300 | 2844 | 1819 | 623 | 30 |
| 47 | 191 | 210 | 400 | 400 | 300 | 1250 | 2866 | 92 | 13 |
| 48 | 187 | 184 | 400 | 400 | 300 | 1420 | 3236 | 99 | 17 |

We claim:

1. A process of preparing di($C_1$-$C_{12}$) alkyl disulfides comprising feeding a $C_1$-$C_{12}$ alkyl alcohol hydrogen sulfide in a molar ratio of 1:2 to 1:20 into contact with a solid, particulate catalyst in a first reaction zone at a catalyst temperature ranging from about 100° to about 500° C. to thereby produce crude alkyl mercaptan, continuously separating water from said crude alkyl mercaptan, and continuously reacting said crude alkyl mercaptan in the vapor phase with molten sulfur in a second reaction zone at a molar ratio of from 1:0.05 to 1:2 in contact with a solid, particulate Type X or Y zeolite catalyst containing from 3 to 13% by weight of an alkali metal, expressed as Me$_2$O, said catalyst having a temperature ranging from about 125° to about 400° C., to thereby continuously produce a di ($C_1$-$C_{12}$) alkyl disulfide.

2. The process of claim 1 wherein the temperature in said second reaction zone ranges from about 125° to about 225° C., the pressure for the reaction in said zone ranges from atmospheric to about 600 psig, and the reaction in said zone proceeds at a molar velocity of 100 to 2000 gram-moles of alkyl mercaptan per kilogram of catalyst per 24 hours.

3. The process of claim 2 wherein said alkyl alcohol has from 1 to 4 carbon atoms.

4. The process of claim 3 wherein said zeolite is a Type Y zeolite containing 5 to 13% by weight of sodium expressed as Na$_2$O.

5. The process of claim 4 wherein said mercaptan and sulfur are reacted at a molar ratio of from 1:0.05 to 1:1, at a pressure within the range of 50 to 375 psig, and at a molar velocity within the range of 750 to 1250 gram-moles of mercaptan per kilogram of catalyst per 24 hours.

6. A process for preparing di ($C_1$-$C_{12}$) alkyl disulfides comprising continuously reacting a $C_1$-$C_{12}$ alkyl mercaptan in the vapor phase with molten sulfur at a molar ratio of from 1:0.05 to 1:2 in contact with a solid particulate Type X or Y zeolite catalyst containing from 3 to 13% by weight of an alkali metal expressed as Me$_2$O, and recovering a di ($C_1$-$C_{12}$) alkyl disulfide product.

7. The process of claim 6 wherein said temperature ranges from about 125° to about 400° C., the pressure for the reaction ranges from atmospheric to about 600 psig, and the reaction proceeds at a molar velocity of 100 to 2000 gram-moles of alkyl mercaptan per kilogram of catalyst per 24 hours.

8. The process of claim 7 wherein said alkyl mercaptan has from 1 to 4 carbon atoms and the reaction temperature ranges from about 125° to about 225° C.

9. The process of claim 8 wherein said zeolite is a Type Y zeolite containing from 5 to 13% by weight of sodium expressed as Na$_2$O.

10. The process of claim 9 wherein said mercaptan and sulfur are reacted at a molar ratio of from 1:0.05 to 1:1 at a pressure within the range of 50 to 375 psig, and at a molar velocity within the range of 750 to 1250 gram-moles of mercaptan per kilogram of catalyst per 24 hours.

* * * * *